United States Patent
Duffy et al.

(10) Patent No.: US 10,359,371 B2
(45) Date of Patent: Jul. 23, 2019

(54) DETERMINING ONE OR MORE CHARACTERISTICS OF A PATTERN OF INTEREST ON A SPECIMEN

(71) Applicant: KLA-Tencor Corporation, Milpitas, CA (US)

(72) Inventors: Brian Duffy, San Jose, CA (US); Ashok Kulkarni, San Jose, CA (US); Michael Lennek, Sunnyvale, CA (US); Allen Park, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 33 days.

(21) Appl. No.: 15/243,809

(22) Filed: Aug. 22, 2016

(65) Prior Publication Data
US 2017/0059491 A1 Mar. 2, 2017

Related U.S. Application Data

(60) Provisional application No. 62/209,231, filed on Aug. 24, 2015.

(51) Int. Cl.
| | | |
|---|---|---|
| G06K 9/64 | (2006.01) | |
| G06T 7/00 | (2017.01) | |
| G01N 21/95 | (2006.01) | |
| H01L 21/66 | (2006.01) | |
| G01N 21/956 | (2006.01) | |
| G05B 19/418 | (2006.01) | |

(52) U.S. Cl.
CPC ... *G01N 21/95607* (2013.01); *G01N 21/9501* (2013.01); *G05B 19/41875* (2013.01); *G06K 9/64* (2013.01); *G06T 7/001* (2013.01); *H01L 22/20* (2013.01); *G01N 2021/95615* (2013.01); *G01N 2021/95676* (2013.01); *G06T 2207/30148* (2013.01); *H01L 22/12* (2013.01)

(58) Field of Classification Search
None
See application file for complete search history.

(56) References Cited

U.S. PATENT DOCUMENTS

| | | | |
|---|---|---|---|
| 6,240,208 B1 * | 5/2001 | Garakani | G06K 9/4609 |
| | | | 382/160 |
| 6,248,602 B1 | 6/2001 | Bode et al. | |
| 6,810,139 B2 | 10/2004 | Smilansky et al. | |
| 6,902,855 B2 | 6/2005 | Peterson et al. | |

(Continued)

OTHER PUBLICATIONS

P. Mitra, C. A. Murthy and S. K. Pal, "Density-based multiscale data condensation," in IEEE Transactions on Pattern Analysis and Machine Intelligence, vol. 24, No. 6, pp. 734-747, Jun. 2002.*

(Continued)

*Primary Examiner* — Kim Y Vu
*Assistant Examiner* — Nathan J Bloom
(74) *Attorney, Agent, or Firm* — Ann Marie Mewherter (57) ABSTRACT

Methods and systems for determining characteristic(s) of patterns of interest (POIs) are provided. One system is configured to acquire output of an inspection system generated at the POI instances without detecting defects at the POI instances. The output is then used to generate a selection of the POI instances. The system then acquires output from an output acquisition subsystem for the selected POI instances. The system also determines characteristic(s) of the POI using the output acquired from the output acquisition subsystem.

27 Claims, 2 Drawing Sheets

(56) References Cited

U.S. PATENT DOCUMENTS

| | | | |
|---|---|---|---|
| 6,988,017 B2 | 1/2006 | Pasadyn et al. | |
| 7,418,124 B2 | 8/2008 | Peterson et al. | |
| 7,487,054 B2 | 2/2009 | Ayala et al. | |
| 7,570,796 B2 | 8/2009 | Zafar et al. | |
| 7,676,077 B2 | 3/2010 | Kulkarni et al. | |
| 7,711,514 B2 | 5/2010 | Park et al. | |
| 7,769,225 B2 | 8/2010 | Kekare et al. | |
| 8,041,106 B2 | 10/2011 | Pak et al. | |
| 8,126,255 B2 | 2/2012 | Bhaskar et al. | |
| 8,213,704 B2 | 7/2012 | Peterson et al. | |
| 8,386,401 B2 | 2/2013 | Virkar et al. | |
| 8,498,468 B1* | 7/2013 | Volk | G06T 7/001 382/144 |
| 8,559,001 B2 | 10/2013 | Chang et al. | |
| 8,611,639 B2 | 12/2013 | Kulkarni et al. | |
| 8,664,594 B1 | 4/2014 | Jiang et al. | |
| 8,692,204 B2 | 4/2014 | Kojima et al. | |
| 8,698,093 B1 | 4/2014 | Gubbens et al. | |
| 8,716,662 B1 | 5/2014 | MacDonald et al. | |
| 8,938,695 B1 | 1/2015 | Juang et al. | |
| 9,098,891 B2 | 8/2015 | Kulkarni et al. | |
| 9,138,624 B2 | 11/2015 | Karsenti et al. | |
| 2004/0126909 A1* | 7/2004 | Obara | G06T 7/0004 438/14 |
| 2007/0288219 A1* | 12/2007 | Zafar | G03F 1/84 703/14 |
| 2009/0238441 A1* | 9/2009 | Yamashita | G06T 7/001 382/144 |
| 2010/0138026 A1 | 6/2010 | Kaushal et al. | |
| 2012/0268735 A1 | 10/2012 | Chen et al. | |
| 2012/0327212 A1* | 12/2012 | Kitahashi | H01J 37/28 348/80 |
| 2013/0035876 A1 | 2/2013 | Huang et al. | |
| 2014/0105482 A1 | 4/2014 | Wu et al. | |
| 2014/0241610 A1 | 8/2014 | Duffy et al. | |
| 2014/0270474 A1 | 9/2014 | Huang et al. | |
| 2014/0301630 A1* | 10/2014 | Kulkarni | G06T 7/0004 382/149 |
| 2014/0376801 A1 | 12/2014 | Karsenti et al. | |
| 2015/0154746 A1 | 6/2015 | Zafar et al. | |
| 2016/0025648 A1 | 1/2016 | Duffy et al. | |
| 2016/0116420 A1 | 4/2016 | Duffy et al. | |
| 2016/0150191 A1 | 5/2016 | Karsenti et al. | |
| 2016/0305892 A1* | 10/2016 | Tsuchiya | G01N 21/956 |
| 2016/0341791 A1 | 11/2016 | Duffy | |

OTHER PUBLICATIONS

Chow T.W.S., Huang D. (2008) Data Reduction for Pattern Recognition and Data Analysis. In: Fulcher J., Jain L.C. (eds) Computational Intelligence: A Compendium. Studies in Computational Intelligence, vol. 115. Springer, Berlin, Heidelberg.*

International Search Report for PCT/US2016/048199 dated Nov. 18, 2016.

Written Opinion for PCT/US2016/048199 dated Nov. 18, 2016.

* cited by examiner

DETERMINING ONE OR MORE CHARACTERISTICS OF A PATTERN OF INTEREST ON A SPECIMEN

BACKGROUND OF THE INVENTION

1. Field of the Invention

The present invention generally relates to methods and systems for determining one or more characteristics of a pattern of interest on a specimen.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Defect review typically involves re-detecting defects detected as such by an inspection process and generating additional information about the defects at a higher resolution using either a high magnification optical system or a scanning electron microscope (SEM). Defect review is therefore performed at discrete locations on the wafer where defects have been detected by inspection. The higher resolution data for the defects generated by defect review is more suitable for determining attributes of the defects such as profile, roughness, more accurate size information, etc.

Metrology processes are also used at various steps during a semiconductor manufacturing process to monitor and control the process. Metrology processes are different than inspection processes in that, unlike inspection processes in which defects are detected on a wafer, metrology processes are used to measure one or more characteristics of the wafer that cannot be determined using currently used inspection tools. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

Metrology processes are also different than defect review processes in that, unlike defect review processes in which defects that are detected by inspection are re-visited in defect review, metrology processes may be performed at locations at which no defect has been detected. In other words, unlike defect review, the locations at Which a metrology process is performed on a wafer may be independent of the results of an inspection process performed on the wafer. In particular, the locations at which a metrology process is performed may be selected independently of inspection results. In addition, since locations on the wafer at which metrology is performed may be selected independently of inspection results, unlike defect review in which the locations on the wafer at which defect review is to be performed cannot be determined until the inspection results tor the wafer are generated and available for use, the locations at which the metrology process is performed may be determined before an inspection process has been performed on the wafer.

While it is true that metrology is generally inspection independent and mostly driven by sites that are either critical or friendly for measuring morphology of polygons and defect review is generally inspection dependent and driven by sites at which defects have been detected, that may not always be the case. For example, in the case of inspection driven metrology, inspection results can be used to guide selecting sites that are abnormal from all available metrology sites. In another example, review can also be performed without inspection by using sites selected by taking simulation or design driven sites and then using the defect review tool to simply collect images for those designated sites. Examples of such methods and systems are illustrated in U.S. Pat. Nos. 7,711,514 to Park et al, issued on May 4, 2010, and 8,559,001 to Chang et al. issued on Oct. 15, 2013, both of which are incorporated by reference as if fully set forth herein.

In general, defect detection is performed with inspection tools as described above and then additional measurements such as critical dimension (CD) measurements performed with a SEM are performed on a fixed sample of locations. There are, however, a number of disadvantages for the currently used methods and systems for generating a sample for defect review or metrology, For example, sources of variation that impact yield relevant attributes of product circuit patterns may not be practically observable due to substantially low area and pattern coverage of CD SEMs and insufficient sensitivity of inspection tools that use thresholding techniques.

Accordingly, it would be advantageous to develop systems and methods for determining one or more characteristics of a pattern of interest on a specimen that do not have one or more of the disadvantages described above.

SUMMARY OF THE INVENTION

The following description of various embodiments is not to be construed in any way as limiting the subject matter of the appended claims.

One embodiment relates to a system configured to determine one or more characteristics of a pattern of interest (POI) on a specimen. The system includes an output acquisition subsystem that includes at least an energy source and a detector. The output acquisition subsystem is configured to direct energy generated by the energy source to a specimen while the detector detects energy from the specimen and generates output responsive to the detected energy. The system also includes a computer subsystem that includes one or more processors configured to execute instructions from a memory medium. The computer subsystem is configured for acquiring output of an inspection system generated by the inspection system for at least a majority of instances of a POI on the specimen and stored in a computer-readable storage medium. The inspection system acquires the output at a resolution that is lower than a resolution of the output acquisition subsystem. The inspection system stores the output acquired at the at least the majority of instances regardless of characteristics of the output. The computer subsystem is also configured for selecting one or more of the at least the majority of instances at which the output is generated by the output acquisition subsystem. The selecting is performed based on the characteristics of the output of the inspection system. In addition, the computer subsystem is configured for acquiring the output generated by the output acquisition subsystem for the selected one or more of the at least the majority of instances. The resolution of the output acquisition subsystem with which the output is acquired at the selected one or more of the at least the majority of instances is higher than the resolution of the inspection system. The system is further configured for determining one or more characteristics of the POI based on the output of the output acquisition subsystem at the selected one or more of the at least the majority of instances. The system may be further configured as described herein.

Another embodiment relates to a computer-implemented method for determining one or more characteristics of a POI on a specimen. The method includes acquiring output of an inspection system generated by the inspection system for at least a majority of instances of a POI on a specimen and stored in a computer-readable storage medium. The inspection system acquires the output at a resolution that is lower than a resolution of an output acquisition subsystem. The inspection system stores the output acquired at the at least the majority of instances regardless of characteristics of the output. The output acquisition subsystem includes at least an energy source and a detector. The output acquisition subsystem is configured to direct energy generated by the energy source to the specimen while the detector detects energy from the specimen and generates output responsive to the detected energy. The method also includes selecting one or more of the at least the majority of instances at which the output is generated by the output acquisition subsystem. The selecting is performed based on the characteristics of the output of the inspection system. In addition, the method includes acquiring the output generated by the output acquisition subsystem for the selected one or more of the at least the majority of instances. The resolution of the output acquisition subsystem with which the output is acquired at the selected one or more of the at least the majority of instances is higher than the resolution of the inspection system. In addition, the method includes determining one or more Characteristics of the POI based on the output of the output acquisition subsystem at the selected one or more of the at least the majority of instances. Acquiring the output of the inspection system, selecting the one or more of the at least the majority of instances, acquiring the output generated b the output acquisition subsystem, and determining the one or more characteristics are performed by a computer subsystem coupled to the output acquisition subsystem. The computer subsystem includes one or more processors configured to execute instructions from a memory medium.

Each of the steps of the method described above may be further performed as described further herein. In addition, the embodiment of the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for determining one or more Characteristics of a POI on a specimen. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Further advantages of the present invention will become apparent to those skilled in the art with the benefit of the Wowing detailed description of the preferred embodiments and upon reference to the accompanying drawings in which.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The terms "design" and "design data" as used herein generally refer to the physical design (layout) of an IC and data derived from the physical design through complex simulation or simple geometric and Boolean operations. In addition, an image of a reticle acquired by a reticle inspection system and/or derivatives thereof can be used as a "proxy" or "proxies" for the design. Such a reticle image or a derivative thereof can serve as a substitute for the design layout in any embodiments described herein that use a design. The design may include any other design data or design data proxies described in commonly owned U.S. Pat. Nos. 7,570,796 issued on Aug. 4, 2009 to Zafar et al. and 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In general, however, the design information or data cannot be generated by imaging a wafer with a wafer inspection system. For example, the design patterns formed on the wafer may not accurately represent the design for the wafer and the wafer inspection system may not be capable of generating images of the design patterns formed on the wafer with sufficient resolution such that the images could be used to determine information about the design for the wafer. Therefore, in general, the design information or design data cannot be generated using a physical wafer, In addition, the "design" and "design data" described herein refers to information and data that is generated by a semiconductor device designer in a design process and is therefore available for use in the embodiments described herein well in advance of printing of the design on any physical wafers.

Turning now to the drawings, it is noted that the figures are not drawn to scale. In particular, the scale of some of the elements of the figures is greatly exaggerated to emphasize characteristics of the elements. It is also noted that the figures are not drawn to the some scale. Elements shown in more than one figure that may be similarly configured have been indicated using the same reference numerals. Unless otherwise noted herein, any of the elements described and shown may include any suitable commercially available elements.

One embodiment relates to a system configured to determine one or more characteristics of a pattern of interest (POI) on a specimen. The embodiments described herein are configured in general for pattern mapping methodology and supporting infrastructure. For example, the embodiments described herein are generally configured for acquiring and analyzing patterning-related optical signals on a substantial portion of all POI instances within a semiconductor chip in combination with high resolution measurements of a site sample drawn from the optical data. This capability is relevant to engineer learning (discovery) and production monitoring.

The system includes an output acquisition subsystem that includes at least an energy source and a detector. The output acquisition subsystem is configured to direct energy generated by the energy source to a specimen while the detector detects energy from the specimen and generates output responsive to the detected energy.

In one embodiment, the specimen is a wafer. In another embodiment, the specimen is a reticle. The wafer and the reticle may include any wafer and reticle known in the art. In general, the embodiments described herein may be used for specimens such as patterned semiconductor wafers or reticles or other substrates requiring substantially high precision patterning. The semiconductor wafers and reticles and other substrates may be patterned in any suitable manner. The specimen may also have been subjected to one or more design of experiments (DOEs). For example, the DOEs may include process window qualification (PWQ). PWQ may be performed as described in U.S. Pat. Nos. 6,902,855 to Peterson et al. issued on Jun. 7, 2005, 7,418,124 to Peterson et al. issued on Aug. 26, 2008, 7,769,225 to Kekare et al. issued on Aug. 3, 2010, 8,041,106 to Pak et al. issued on Oct. 18, 2011, and 8,213,704 to Peterson et al. issued on Jul. 3, 2012, which are incorporated by reference as if fully set forth herein. The embodiments described herein may include any step(s) of any method(s) described in these patents and may be further configured as described in these patents. A PWQ wafer may be printed as described in these patents.

Figure 1:
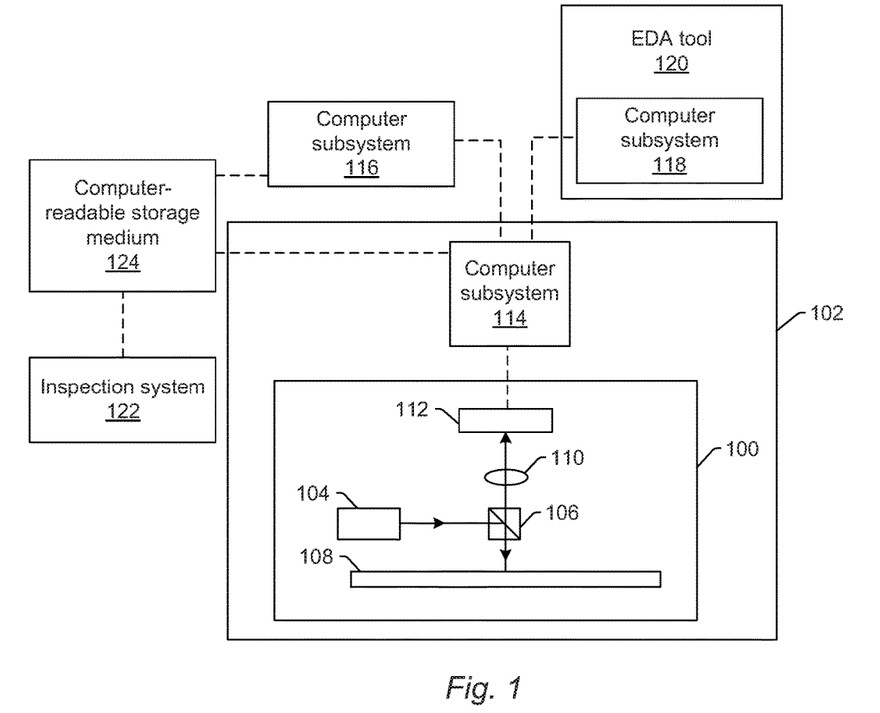
FIGS. 1 and 1a are schematic diagrams illustrating side views of embodiments of a system configured to determine one or more characteristics of a pattern of interest (POI) on a specimen.

In one embodiment, the energy source is a light source, and the energy detected by the detector includes light. In this manner, the output acquisition subsystem may be configured as an optical or light-based output acquisition subsystem. One embodiment of such an output acquisition subsystem is shown in FIG. 1 as output acquisition subsystem 100 of system 102. The output acquisition subsystem is configured for directing light to a specimen and detecting light from the specimen. For example, as shown in FIG. 1, the output acquisition subsystem includes light source 104, which may include any suitable light source known in the art. In one example, the light source may be a broadband plasma (BBP) light source, which may be any suitable such tight source known in the art. The light that is directed to the specimen may include monochromatic light, polychromatic light, or broadband light.

Light from the light source may be directed to beam splitter 106, which may be configured to direct the light from the light source to specimen 108. The light source may be coupled to any other suitable elements (not shown) such as one or more condensing lenses, collimating lenses, relay lenses, objective lenses, apertures, spectral filters, polarizing components and the like. As shown in FIG. 1, the tight may be directed to the specimen at a normal angle of incidence, However, the light may be directed to the specimen at any suitable angle of incidence including near normal and oblique incidence. In addition, the light or multiple light beams may be directed to the specimen at more than one angle of incidence sequentially or simultaneously. The output acquisition subsystem may be configured to scan the light over the specimen in any suitable manner.

Light from specimen 108 may be collected and detected by one or more detectors of the output acquisition subsystem during scanning For example, light reflected from specimen 108 at angles relatively close To normal (i.e., specularly reflected light when the incidence is normal) may pass through beam splitter 106 to lens 110. Lens 110 may include a refractive optical element as shown in FIG. 1. In addition, lens 110 may include one or more refractive optical elements and/or one or more reflective optical elements. Light collected by lens 110 may be focused to detector 112. Detector 112 may include any suitable detector known in the art such as a charge coupled device (CCD) or another type of imaging detector. Detector 112 is configured to generate output that is responsive to the reflected tight collected by lens 110. Therefore, lens 110 and detector 112 form one channel of the output acquisition subsystem. This channel of the output acquisition subsystem may include any other suitable optical components (not shown) known in the art. The output of the detector may include, for example, images, image data, signals, image signals, or any other output that can be generated by a detector suitable for use in a wafer or reticle output acquisition system.

Since the output acquisition subsystem shown in FIG. 1 is configured to detect light specularly reflected from the specimen, the output acquisition subsystem is configured as a bright field (BF) output acquisition subsystem. Such an output acquisition subsystem may, however, also be configured for other types of output acquisition. For example, the output acquisition subsystem shown in FIG. 1 may also include one or more other channels (not shown). The other channel(s) may include any of the optical components described herein such as a lens and a detector, configured as a scattered light channel. The lens and the detector may be further configured as described herein. In this manner, the output acquisition subsystem may also be configured for dark field (DF) output acquisition.

It is noted that FIG. 1 provided herein to generally illustrate a configuration of a light-based output acquisition subsystem that may be included in the system embodiments described herein. Obviously, the output acquisition subsystem configuration described herein may be altered to optimize the performance of the output acquisition subsystem as is normally performed when designing a commercial output acquisition system. In addition, the systems described herein may be implemented using an existing output acquisition subsystem (e.g., by adding functionality described herein to an existing output acquisition system) such as the SpectraShape family of tools and the Archer series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system. The system shown in FIG. 1 may be further configured as described herein.

Although the system is described above as being an optical or light-based output acquisition system, the output acquisition subsystem may be an electron beam-based subsystem. In one such embodiment, the energy source is an electron beam source, and the energy detected by the detector includes electrons. In one such embodiment shown in FIG. 1a, the output acquisition subsystem includes electron column 123 coupled to computer subsystem 125.

Figure 1A:
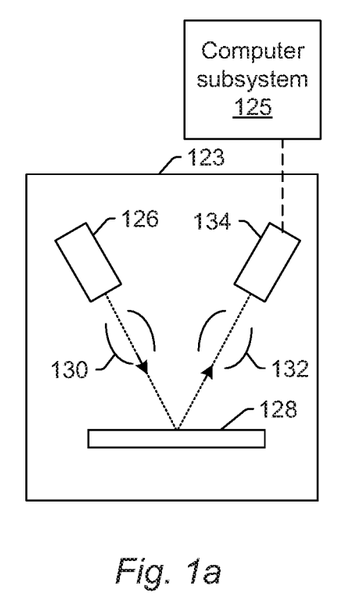

As also shown in FIG. 1a, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen secondary electrons) may be focused by one or more elements 132 to detector 134. One or more elements 132 may include, for example, a scanning subsystem, which may be the same scanning subsystem included element(s) 130.

The electron column may include any other suitable elements known in the art. In addition, the electron column may be further configured as described in U.S. Pat. Nos. 8,664,594 issued Apr. 4, 2014 to Jiang et al., 8,692,204 issued Apr. 8, 2014 to Kojima et al, 8,698,093 issued Apr. 15, 2014 to Gubbens et al., and 8,716,662 issued May 6, 2014 to MacDonald et al., which are incorporated by reference as if fully set forth herein.

Although the electron column is shown in FIG. 1a as being configured such that the electrons are directed to the specimen at an oblique angle of incidence and are scattered from the specimen at another oblique angle, it is to be understood that the electron beam may be directed to and scattered from the specimen at any suitable angles.

Computer subsystem 125 may be coupled to detector 134 as described herein. The detector may detect electrons returned from the surface of the specimen thereby forming electron beam images of the specimen. The electron beam images may include any suitable electron beam images. Computer subsystem 125 may be configured to perform one or more functions described herein using output generated by detector 134. Computer subsystem 125 may be configured to perform any additional step(s) described herein, It is noted that FIG. 1a is provided herein to generally illustrate a configuration of an electron beam-based output acquisition subsystem that may be included in the system embodiments described herein. As with the optical subsystem described above, the electron beam-based subsystem configuration described herein may be altered to optimize the performance of the output acquisition subsystem as is normally performed when designing a commercial output acquisition system. In addition, the systems described herein may be implemented using an existing output acquisition subsystem (e.g., by adding functionality described herein to an existing output acquisition system) such as the eDR-xxxx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system. The system shown in FIG. 1a may be further configured as described herein.

Although the output acquisition subsystem is described above as being a light-based or electron beam-based output acquisition subsystem, the output acquisition subsystem may be an ion beam-based output acquisition subsystem.

For example, in one embodiment, the energy source is a charged particle beam source, and the energy detected by the detector includes charged particles. Such an output acquisition subsystem may be configured as shown in FIG. 1a except that the electron beam source may be replaced with any suitable ion beam source known in the art. In addition, the output acquisition subsystem may be any other suitable ion beam-based output acquisition subsystem such as those included in commercially available focused ion beam (FIB) systems, helium ion microscopy (HIM) systems, and secondary ion mass spectroscopy (SIMS) systems.

The system includes a computer subsystem configured for performing a number of functions described further herein. The computer subsystem(s) may also be referred to herein as computer system(s). The computer subsystem(s) or system (s) may take various forms, including a personal computer system, image computer, mainframe computer system, workstation, network appliance, Internet appliance, or other device. In general, the term "computer system" may be broadly defined to encompass any device that includes one or more processors configured to execute instructions from a memory medium. The computer subsystem(s) or system(s) may also include any suitable processor known in the art such as a parallel processor. In addition, the computer subsystem(s) or system(s) may include a computer platform with high speed processing and software, either as a stand-alone or a networked tool.

The computer subsystem may be included in a system that includes the output acquisition subsystem. For example, the computer subsystem may be computer subsystem 114 coupled to output acquisition subsystem 100 shown in FIG. 1 and/or computer subsystem 125 shown in FIG. 1a. Computer subsystem 114 may be coupled to detector 112 and any other detectors of the output acquisition subsystem such that the computer subsystem can receive output (e.g., images) generated by the detector(s). In a similar manner, computer subsystem 125 may be coupled to detector 134 and any other detectors of the output acquisition subsystem such that the computer subsystem can receive output (e.g., images) generated by the detector(s).

The computer subsystem may also or alternatively include a stand-alone type computer system. For example, as shown in FIG. 1, the computer subsystem may include computer subsystem 116 that is not part of a system that includes the output acquisition subsystem.

The computer subsystem may further include a computer subsystem that is part of an electronic design automation (EDA) tool, and the output acquisition subsystem described further herein is not part of the EDA tool. For example, as shown in FIG. 1, the computer subsystem described above may be computer subsystem 118 included in EDA tool 120, The FDA toot and the computer subsystem included in such a tool may include any commercially available FDA tool that can be configured as described herein. Therefore, the computer subsystem(s) that are configured as described herein may be separate from an output acquisition system that is used to acquire output for the specimen.

If the system includes more than one computer subsystem, then the different computer subsystems may be coupled to each other such that images, data, information, instructions, etc. can be sent between the computer subsystems. For example, computer subsystem 114 may be coupled to stand-alone computer subsystem 116 and/or computer subsystem 118 of EDA tool 120 as shown by the dashed lines in FIG. 1 by any suitable transmission media, which may include any suitable wired and/or wireless transmission media known in the art. Two or more of such computer subsystems may also be effectively coupled by a shared computer-readable storage medium (not shown) such as a fab database. If the system includes multiple computer subsystems, then different computer subsystems may be configured to perform different functions described further herein. Alternatively, only one of the computer subsystems shown in FIG. 1 may be configured to perform all of the functions described further herein.

As described further herein, a number of steps or functions may be performed based on POIs and one or more instances of a POI. In some instances, the embodiments described herein may be configured to identify the POIs and the instance of the POIs on the specimen. However, in other instances, information about the POIs and the instances of the POIs on the specimen may be acquired from another system or method. In either case, the locations of the POIs can come from one or more sources. Sources of the POI information may include a physical design (layout) database or its derivatives, which could include modeling, Another source of the POI information may include other reticle or wafer analysis including process window analysis. An additional source of the POI information may include electrical testing results of wafers with identical or similar patterns. Sources of the POI information may also include physical failure analysis. There are also many other methods for deciding which POIs to use in the embodiments described herein, examples of which are described in U.S. Pat. Nos. 7,676,077 to Kulkarni et al. issued on Mar. 9, 2010, and 8,611,639 issued on Dec. 17, 2013 to Kulkarni et al., which are incorporated by reference as if fully set forth herein. The embodiments described herein may be further configured as described in these patents.

The computer subsystem is configured for acquiring output of an inspection system generated by the inspection system for at least a majority of instances of a P0I on the specimen and stored in a computer-readable storage medium. For example, as shown in FIG. 1, inspection system 122 may generate output, for a specimen and therefore instances of POIs on the specimen and may store the output in computer-readable storage medium 124. The inspection system may be coupled to the computer-readable storage medium as described further herein, e.g., by one or more transmission media which may include wired and wireless transmission media. The computer-readable storage medium may include any computer-readable storage medium described herein. The computer subsystems described herein may be coupled to the computer-dable storage medium as described further herein, e.g., by one or more transmission media such that the computer subsystem can acquire the output of the inspection system. For example, as shown in FIG. 1, computer subsystems 114 and 116 may be coupled to computer-readable storage medium 124 as shown by the dashed lines, which may include one or more of the transmission media described herein. The inspection system and the computer-readable storage medium may be coupled in a similar manner to computer subsystem 125 shown in FIG. 1a.

The optical or electron beam signals may be generated by the inspection system for a substantial portion or all of the POI instances on a specimen. In this manner, the systems may acquire patterning related optical or electron beam signals on a substantial portion or all of the POI instances on a specimen. The output of the inspection system that is stored by the inspection system may include images generated for the specimen. In this manner, the images from which characteristics of the specimen are being generated may be stored on a storage device. The computer subsystem may then acquire from the computer-readable storage medium the output generated by the inspection system for the at least the majority of the POI instances. In this manner, the computer subsystem may be configured for acquisition of attributes from optical or electron beam signals at a substantial fraction of all POI instances. Although the output of the inspection system may be acquired from the computer-readable storage medium, the physical specimen may be available for further analysis When a storage device is used.

The inspection system acquires the output at a resolution that is lower than a resolution of the output acquisition subsystem. For example, the inspection system may be configured as a substantially high speed optical image acquisition and analysis system (e.g., an inspection system that includes a BBP light source). Inspection system 122 may include any suitable commercially available inspection system such as the 29xx/39xx series of tools that are commercially available from KLA-Tencor or any other suitable inspection system known in the art. In addition, inspection system 122 may be configured as an optical or light-based inspection system or an electron beam-based inspection system, which may include any suitable electron beam-based inspection system known in the art.

The inspection system stores the output acquired at the at least the majority of instances regardless of characteristics of the output. In one embodiment, the inspection system identifies the locations of the at least the majority of the instances of the POI on the specimen without detecting defects on the specimen. In other words, the inspection system does not apply a defect detection algorithm to the output generated for the specimen to detect defects on the wafer, which are then labeled as areas or patterns of interest. Instead, the inspection system may acquire the output at the POI instances without regard to the output at the POI instances (i.e., regardless of whether or not it is above a defect detection threshold). Therefore, the output acquisition performed by the inspection system for the POI instances may be considered un-thresholded in that the output that is acquired and stored by the inspection system is not just output that is above a defect detection threshold. In this manner, the analysis of the POI instances may be delayed compared to normal output acquisition using an inspection system, where the output is analyzed as the output is generated. In addition, analysis of the output acquired at the POI instances may be delayed until all output for the wafer is collected. In this manner, the output acquisition process may be different from normal output acquisition performed by an inspection system because judgment about what is an outlier is delayed until output for the whole specimen at least a substantial portion of the specimen) is collected. Therefore, acquiring and storing the inspection output for delayed analysis as described herein provides flexible analysis and detection of outliers in the output. In addition, the output analysis performed for the output generated by the inspection system for the POI instances may be unconstrained in x and y.

In one embodiment, computer-readable storage medium 124 shown in FIG. 1 is configured as a virtual inspector (VI). The VI may be configured as described in commonly assigned U.S. Pat. No. 8,126,255 issued on Feb. 28, 2012 to Bhaskar et al. and U.S. Patent Application Publication Nos. 2014/0241610 by Duffy et al. published on Aug. 28, 2014, and 2016/0025648 by Duffy et al. published on Jan. 28, 2016, all of which are incorporated by reference as if fully set forth herein. In other words, in some embodiments, the computer-readable storage medium may be configured as a virtual inspection system. In these embodiments, the output of the inspection system may be output that was previously generated by one or more detectors of an optical or electron beam inspection system and that is stored in the virtual inspection system, and the virtual inspection system may replay the stored output as though the specimen is being scanned. In this manner, scanning the specimen with a virtual inspection system may appear to be the same as though a physical specimen is being scanned with an actual inspection system, while, in reality, the scanning involves simply replaying output for the specimen in the same manner as the specimen may be scanned. The embodiments described herein may be further configured as described in the patent and patent applications incorporated by reference above.

The volume of output (or data points) generated by the inspection system may be in the hundreds of billions. For example, each POI may have millions of instances on a given layer of a chip. In addition, there may be thousands of POI types on a given layer of a chip and 50 to hundreds of chips per wafer. This volume of data may be generated for each of several passes in different optical modes. Each pass may expected to be accomplished in about an hour. In addition, although the embodiments described herein are described with respect to a POI, it is to be understood that the embodiments described herein may be configured to perform the functions described herein for more than one type of POI simultaneously or serially. In this manner, the embodiments described herein may be configured to analyze all POI types on a specimen. However, regardless of whether the analysis is performed for multiple POI types simultaneously or serially, the analysis may be performed for each POI type separately (i.e., only the output for one POI type may be used when analyzing that one POI type).

When considering the POIs identifying the POIs in the output of the inspection system), it may be important to take into consideration how the POIs may be affected by other structures in their proximity. For example, there may be optical proximity effects of an image acquisition system that are considered. In one such example, two physically identical POI instances placed in different surrounding neighborhoods in the chip layout could get different attribute values if the neighboring structure differences are close enough to impact the image acquired by the system (optical proximity effects of the image acquisition system). The practical implication is that the methodology may take such effects into consideration so that analysis is segmented, not just for each POI, but for POI plus surrounding neighborhood. In another example, the proximity effects of the process used to make the specimen may be taken into consideration. In one such example, two identical as drawn in the design) instances placed in the context of different surrounding neighborhood structures within a distance known to cause process optical proximity effects (e.g., due to the lithography process) may be modified with layout changes to strive to make the resulting on-wafer structures identical (this is optical proximity correction (OPC)). In a further example, OPC variations applied to different instances of the same POI with identical intent may be considered. In one such example, the OPC process may be executed by software that does not necessarily perform in a repeatable manner. It is possible to have two identical layout instances that get altered differently due to quirks in the OPC process. It may be important to know this so that differences in OPC execution are not mistaken for process variation.

In another embodiment, the inspection system is an optical inspection system. In a further embodiment, the inspection system is an electron beam-based inspection system. The optical or electron beam inspection system may also be an image-based inspection system. The optical or electron beam inspection system may have a flexible optical configurability. The inspection or electron beam system may include a substantially high speed stage. In addition, the inspection system may use smaller pixels than the optical spot size of the tool to facilitate substantially high accuracy and precision alignment to design. In contrast, in currently used systems and methods, the care areas are typically limited to the size of the optical spot of the energy source at the plane of the specimen.

The computer subsystem is also configured for selecting one or more of the at least the majority of instances at which the output is generated by the output acquisition subsystem. The selecting is performed based on the characteristics of the output of the inspection system. The characteristics of the output (e.g., image attributes) may be calculated for each targeted POI location. Some or all of the characteristics image attributes) may be calculated on an absolute basis or by comparison to a reference image (e.g., a difference image), The reference image may be acquired using the specimen or from a storage device. Location accuracy of the reference location may also be as precise (e.g., with sub-pixel accuracy) as described further herein. The characteristics of the output of the inspection system (e.g., image attributes) are preferably substantially related to one or more physical attributes of interest. The characteristics may be analyzed in some manner prior to selecting one or more of the instances based on the characteristics. In particular, the characteristics may be analyzed collectively (by analyzing a combination of the characteristics determined for more than one instance of the POI). For example, a histogram of a characteristic of the output generated for multiple instances of a may be determined, and then the selecting may be performed based on the determined histogram. The selecting may be performed according to any other embodiments described herein.

In this manner, the computer subsystem may be configured to generate a sample of sites drawn from the data generated by the inspection system and acquired by the computer subsystem. As such, the sample plan for the further analysis may depend on the inspection system's results. In other words, the computer subsystem described herein may be configured for coupling the signals from an inspection system to another output acquisition subsystem (e.g., a scanning electron microscope (SEM)) for adaptive measurement location sampling. Therefore, the embodiments described herein may serve as a pointer for higher resolution instruments for gathering additional data from the specimen in order to draw more deterministic conclusions.

The sampling for the higher resolution output acquisition subsystem may include combining inspection image attributes. The sampling for the higher resolution analysis may include spatial analysis of the inspection system output. Spatial analysis may include hierarchical die, reticle, wafer level attribute modeling (such as that performed by commercially available products such as KT Analyzer that is commercially available from KLA-Tencor). Spatial analysis may also or alternatively include localized aggregation of data points (e.g., on a fixed grid of cells) for noise averaging.

The quantity of locations of interest may include a substantial portion of POI instances on the specimen (i.e., at least a majority of instances). In addition, the at least the majority of instances of the POI and the selecting one or more instances of the POI may span an area on the specimen that covers an entirety of the specimen or only a portion of the specimen. For example, the at least the majority of the instances of the POI may include every single instance of the POI on the specimen such that the POI instances and the selected one or more POI instances span an area on the specimen that is approximately equal to the entire area on the specimen (or the entire patterned areas on the specimen). In this manner, the output acquisition plan may include all instances of a given POI. Alternatively, the at least the majority of the instances of the POI and the selected one or more POI instances may include fewer than all of the POI instances on the specimen and may span an area on the specimen that is less than the entirety of the specimen. For example, the at least the majority of the instances of the POI and the selected one or more POI instances may be located within only a single die on a specimen such as a wafer, which includes many instances of the die on the specimen. In another example, the at least the majority of the instances of the POI and the selected one or more POI instances may be located within only the scanned portion of the specimen, which may include fewer than all of the instances of the POI in one or more portions of the die(s) formed on the specimen.

In one embodiment, the inspection system identifies the locations of the at least the majority of the instances of the POI on the specimen without detecting defects on the specimen. In one such embodiment, selecting the one or more of the at least the majority of instances is not performed based on defects detected at the instances of the POI. For instance, the nature of defect detection algorithms and the use of thresholding concepts leave sensitivity "on the table." By using an un-thresholded approach, more sophisticated post-processing can be performed for selecting the sites to analyze with a relatively high resolution tool.

In another embodiment, the characteristics of the output of the inspection system include characteristics of raw image data generated by the inspection system for the at least the majority of the instances of the POI. For example, raw image data for a whole specimen, e.g., wafer, may be compressed into data points for each POI instance where a data point includes summary attributes derived from the pixilated image data collected at each POI instance. The basis of an individual data point may be at least one summary attribute drawn from a care area instance.

The computer subsystem is further configured for acquiring the output generated by the output acquisition subsystem for the selected one or more of the at least the majority of instances. The resolution of the output acquisition subsystem with which the output is acquired at the selected one or more of the at least the majority of instances is higher than the resolution of the inspection system. For example, the output acquisition subsystem may be configured as a substantially high resolution measurement system (e.g., a SEM with metrology algorithms). The output acquisition subsystem may be configured to have programmable imaging features (e.g., flexible illumination and/or image acquisition capabilities). The output acquisition subsystem may be configured as a modified defect inspection system. Alternatively, the output acquisition subsystem may be a modified metrology system. The modified system may be multi-purposed (e.g., for the functions described herein and other defect detection or metrology) or dedicated for the functions described herein. In addition, the output acquisition subsystem may be configured to use multiple imaging modes (e.g., multiple optical or electron beam imaging modes) to improve the useable signal of the output acquired by the output acquisition subsystem. The embodiments described herein can also benefit from volumetric and virtual multi-mode methods. The volume of data points generated by the higher resolution system will be a relatively small subset of that from the optical or electron beam inspection system. The data acquisition rate of the output acquisition subsystem may be on the order of thousands of points per hour.

As described herein, the system includes the output acquisition subsystem. Therefore, the embodiments may be configured for direct data acquisition with a tool optimized for this purpose. The embodiments may also be built on top of a VI, which may be configured as described herein. Furthermore, the embodiments may be incorporated into the operation of an existing wafer inspector augmented for this purpose (which may be performed in series or parallel with other defect detection performed for the specimen).

In one embodiment, the instances of the POI on the specimen are located by the inspection system with sub-pixel accuracy. "Sub-pixel" as that term is used herein is generally defined as smaller than a pixel of an image. In this manner, "sub-pixel accuracy" as that term is used herein can be generally defined as the determination of the position of something (e.g. a POI instance) with an error smaller an the size (distance from one side to the other) of a single pixel in the image. In this manner, the embodiments described herein may have substantially high precision location and image acquisition control such that specific POIs can be targeted and analyzed possibly with programmable imaging modes of the type found on a commercially available inspection system such as those available from KLA-Tencor (e.g., various spectral profiles, various illumination apertures, various imaging apertures, pupil shaping options, etc.) where data collection may be performed serially in multiple modes and combined prior to analysis. For example, the location control may make use of NanoPoint technology that is commercially available from KLA-Tencor. In addition, the POI instances can be labeled as care areas with traceability to known portions of a chip design. Furthermore, the motivations for care areas can overlap (i.e., a care area may be labeled as a care area for multiple reasons).

In another embodiment, the output for the selected one or more of the at least the majority of instances is generated by the output acquisition subsystem by locating the selected one or more of the at least the majority of instances with sub-pixel accuracy. In this manner, the embodiments described herein may have substantially high precision location control such that specific POIs can be analyzed. For example, the location control may make use of NanoPoint technology that is commercially available from KLA-Tencor. In this manner, the computer subsystem may use NanoPoint technology in un-thresholded manner to force output acquisition at specified pattern locations (POI) where the care areas are on the order of the process proximity characteristic length (e.g., about 300 nm), the optical proximity effect of a process used to form the patterned structures on the specimen, which is described further herein. For other (non-litho) processes, there are also neighborhood effects (process loading effects) such as chemical-mechanical polishing (CMP) and etch which can have analogous impacts based on the process specifics. When looking for systematic sources of variation with the data described herein, it may be helpful to make use of what is known of these characteristics to help interpret the results.

The computer subsystem is also configured for determining one or more characteristics of the POI based on the output of the output acquisition subsystem at the selected one or more of the at least the majority of instances. In this manner, the embodiments described herein may be configured for acquiring and analyzing patterning related output (e.g., optical signals) generated for a substantial portion or all of the POI instances on a specimen in combination with high resolution measurements of a site sample drawn from the optical data. For example, the data analysis can be performed on substantial portions of the specimen, up to and including the whole specimen. Therefore, the system may include a substantially high resolution tool (typically but not necessarily electron beam) for final disposition of the POI instances. The determined one or more characteristics of the POI may be further analyzed and reported in any suitable manner by the computer subsystem.

The embodiments described herein, therefore, enable pattern monitoring at "parts per million." For example, the potential hot spots POI instance locations may number in the millions to billions. Characteristics for all or a substantial portion of these hot spots my be acquired and the instances of the hot spots may be filtered. The remaining hot spots, which may number in the hundreds to thousands, may then be reviewed for critical dimension (CD) or other quantifiable characteristics of the patterned structures. In this manner, the selecting and determining steps described herein may essentially involve sampling and metrology.

In some instances, a modeled response for the POIs may be available in advance of data collection. For example, modeling of what the POI would look like when processed and observed through the imaging system of the embodiments described herein may be performed. The attributes may then be calculated from that image. The modeled response may be used in the generation of attributes and/or as a reference. This is analogous to a die-to-database inspection where the reference image is modeled from design. In the present embodiments, the image may be modeled and then summary attributes for each POI can be calculated from that modeled reference image. The results may trigger follow on physical or mathematical operations (including modeling). In addition, a signal threshold may be applied. Furthermore, a data filter may be applied to the output at any stage of the analysis flow.

The output acquisition of the output acquisition subsystem may be adaptive (the next data to collect depends on the previous data). In this manner, the computer subsystem may perform determination of the one or more characteristics of the POI as the output acquisition subsystem generates the output for the selected instances of the POI and the computer subsystem may control that output generation based on the determined one or more characteristics. For example, a probabilistic model of the expected data may be known in advance. Exceptions to the expected data characteristics may factor into the adaptation. The adaptation may be triggered manually or with varying levels of automation. In addition, the analysis plan of the higher resolution output acquisition subsystem may be generated from the physical layout of each POI.

In one embodiment, the one or more characteristics of the POI determined based on the output of the output acquisition subsystem are not detectable in any output generated by the inspection system. For example, the embodiments described herein my advantageously be used to detect low frequency patterning errors that are yield killers, but fall below the sensitivity of conventional optical or electron beam inspection and below the area coverage budget of electron beam inspection (EBI) tools rendering them previously undetectable using currently available methods and systems. In addition, the embodiments described herein can mitigate the issue that arises when relatively low frequency metrology on targets makes assumptions about the relationship between the targets and product geometries as well as the rate at which processes impact patterning variations spatially. Furthermore, on-wafer product chip structure variations may be higher than what is observed on metrology structures customized for specific high precision metrology tools. In addition to the typical use of dedicated metrology structures, the throughput of high precision metrology tools is insufficient for capturing on-chip variance with substantially high confidence. The substantially high area coverage of the inspection system (compared to the output acquisition subsystem) has sufficient signal to relevant process variation and can be leveraged as a pointer for metrology tool sampling. The result is that the output of the inspection system can be extracted for millions of candidate structures in the course of selecting a relatively small number of sites with the highest process variation for sampling.

In another embodiment, the determined one or more characteristics of the POI include one or more quantifiable characteristics of the POI. For example, the embodiments described herein may measure process variations (e.g., CD variations) on structures of interest. In addition, determining the one or more characteristics of the POI may include quantifying observable structure geometry from die-to-die with metrology-like output acquisition subsystems. However, the conclusions drawn from the attributes about the one or more locations may be probabilistic. The characteristics of the POI may be determined from the output using any suitable method and/or algorithm.

In a further embodiment, the system is configured as a metrology system. For example, the further analysis described herein may include high resolution output acquisition which may include metrology. The output acquisition subsystem may be configured for further analysis based on scanning electron optics. In addition, the output acquisition subsystem configured for the further analysis described herein may be configured as a SEM (possibly configured with metrology software and algorithms), transmission electron microscope (TEM), scanning transmission electron microscope (STEM), atomic force microscope (AFM), a focused ion beam (FIB) system (e.g., imaging and/or milling), electron beam inspection (EBI) system, a voltage contrast electron beam system, etc. The systems described herein may be further configured as a SEM as described in U.S. Patent Application Publication No. 2016/0116420 by Duffy et al. published on Apr. 28, 2016, which is incorporated by reference as if fully set forth herein. The systems described herein may also be further configured as a voltage contrast electron beam system, examples of which are described in U.S. patent application Ser. No. 15/136,680, which is incorporated by reference as if fully set forth herein. In addition, the output acquisition subsystem may be calibrated to the higher resolution system to ensure data relevance.

In some embodiments, determining the one or more characteristics is performed based on the output of the output acquisition subsystem at the selected one or more of the at least the majority of instances in combination with the output of the inspection system generated for at least one of the instances of the POI. For example, the embodiments described herein may make use of output of an inspection system that is stored and available for use regardless of whether defects are detected at the POI instances. Therefore, the embodiments described herein essentially can perform delayed analysis of the output of the inspection system. Such delayed analysis provides flexible analysis and/or detection of outliers. In addition, the output analysis performed with the output of the inspection system is unconstrained in x and y. Furthermore, the embodiments described herein afford spatial output analysis flexibility by delaying output disposition until all or a substantial portion of the output is generated (unlike an inspector which analyzes a frame at a time). The ability to design a data processing and storage pipeline as described herein to cope with the substantially high volumes of POI simultaneously may be facilitated by utilizing data compression at the pixel level early in the signal analysis pipeline (e.g., as described further herein, summary attributes may be stored per POI care area). In addition, since the output of the inspection system will be available at the time the output of the output acquisition subsystem is being analyzed, the embodiments described herein may be configured to determine whether there is a correlation between the one or more characteristics determined based on the output of the output acquisition subsystem and the output of the inspection system or the characteristics of the output of the inspection system (e.g., raw image data or attributes of the raw image data).

In another embodiment, determining the one or more characteristics includes determining one or more initial values for the one or more characteristics of the POI based on the output of the output acquisition subsystem at the selected one or more of the at least the majority of instances in combination with a first portion of the output of the inspection system generated for at least one of the instances of the POI and, based on the one or more initial values, selecting a second portion of the output of the inspection system generated for at least one of the instances of the POI stored in the computer-readable storage medium and determining the one or more characteristics of the POI based on the output of the output acquisition subsystem at the selected one or more of the at least the majority of instances in combination with the second portion of the output of the inspection system generated for the at least one of the instances of the POI. In this manner, the further analysis and the optical or electron beam analysis on the stored specimen may overlap in time. In addition, feedback from the further analysis may be used to modify the output acquisition for the stored specimen. The feedback from the higher resolution system may be manual, semiautomatic, or fully automated. The computer subsystem may also be configured for statistical spatial modeling of the output from either (or both) system(s), which may be used for process control. In this manner, the embodiments described herein may be configured for performing SEM analysis in parallel with new optical or electron beam attribute acquisition with the use of a VI.

The output acquisition or subsequent application of it may also leverage metrology (and possibly other) data from other sources. The metrology data may come from special purpose targets on the specimen. The metrology data may also or alternatively come from the reticle(s) used to pattern the wafer. In addition, the metrology data may have been acquired from proxies for the specimen (e.g., test wafers). The metrology data may also or alternatively be acquired electrically. Furthermore, the metrology data may include wafer (e.g., reticle, substrate) geometry data.

The embodiments described herein, therefore, provide approaches to processing data that allow a different and broader set of questions to be answered than is possible with conventional inspection and metrology. For example, users of the embodiments described herein may be interested in iteratively interrogating the optical or electron beam data set a number of different ways through a process of formulating and testing hypotheses using data from one or more of the high resolution instruments described herein in combination with analytical techniques such as forced ranking (information about the tails of the data distribution for a given POI), probabilistic predictions likelihood of being bad), or categorical inspection-like analysis (good/bad determinations). Furthermore, advanced techniques in the machine learning domain may be applied.

In a further embodiment, the computer subsystem is configured for determining a variation in the one or more characteristics of the POI and determining a source of the variation based on the variation. For example, the computer subsystem may be configured for mapping optical or electron beam signals for POI from an inspection system at prescribed locations for source of variation analysis in the manner done for metrology tools. Just as context based inspection (CBI) changed the nature of defect detection, the embodiments described herein have the potential to change the nature of metrology and associated process control methods. In some instances, a variation in the one or more characteristics of the POI may be used to identify unintended changes in the design (e.g., malicious circuit changes). For example, a chip may be intended to have 10 million structures that are identical but several instances may be subversively changed. The embodiments described herein may be used to detect such changes in the design of the chip. In this manner, the embodiments described herein may be used to detect potentially malicious alterations of the circuitry.

In another embodiment, the determined one or more characteristics of the POI correspond to only patterning deviations in the POI. For example, unlike currently used methods and systems, the embodiments described herein may be configured to find outlier patterning deviations only (vs. general purpose wafer inspection which attempts to find any type of defect on a wafer).

The results that are generated based on the determined one or more characteristics of the POI by the computer subsystem may also vary depending on the type of specimen that is being considered. For example, if the specimen is a PWQ wafer, then the computer subsystem may be configured to generate PWQ wafer contour maps for the SEM and optical or electron beam attributes from the same POI. In one such example, the computer subsystem may generate a contour plot for CD, which is determined by the computer subsystem based on the output generated by the output acquisition subsystem, as a function of focus and exposure values (if the wafer is modulated in focus and exposure of a lithography process). The computer subsystem may also generate a contour plot for optical or electron beam parameters generated by an inspection system for the same wafer as a function of focus and exposure values. When there is a correlation between the determined one or more characteristics of the POI and the output generated for the POI by the inspection system, the correlation may be observed by comparison of the different contour plots generated by the computer subsystem. Additional examples of performing PWQ for a specimen can be found in U.S. Patent Application Publication No. 2016/0150191 to Karsenti et al. published on May 26, 2016, which is incorporated by reference as if fully set forth herein. The embodiments described herein may be further configured as described in this patent application publication.

In addition to contour plots (which may also be generated for non-PWQ wafers (e.g., a contour plot may be generated for optical or electron beam signal as a function of die position in x and y and a contour plot may be generated for the determined one or more characteristics as a function of the same die positions)), the results of the determining one or more characteristics of the POI instances may also be output in another format such as color plots, statistics, trending, and custom reports. The results of the determining step may also be exported to other applications for further analysis, reporting, tracking, etc.

The computer subsystem may also perform additional functions for the POI instances based on the output generated by the output acquisition subsystem (possibly in combination with output generated for the POI instances by the inspection system or another system). Examples of such additional functions are described in U.S. Pat. No. 8,611,639 issued on Dec. 17, 2013 to Kulkarni et al., which is incorporated by reference as if fully set forth herein. The embodiments described herein may be further configured as described in this patent. In addition, the embodiments described herein provide methods and systems that can be used to perform the functions described in this patent in a manner exceeding the volume of patterns possible with an existing inspection system. The embodiments described herein may also be further configured as described in U.S. Pat. No. 9,138,624 to Karsenti et al. issued on Nov. 10, 2015, which is incorporated by reference as if fully set forth herein.

As described herein, a significant amount of information and different types of information can be generated for POIs by utilizing the output of an inspection system for the POI instances in combination with analysis of additional output generated for a sample of the POI instances by an output acquisition subsystem at a higher resolution, In addition to the data processing already described, the computer subsystem may also be configured to determine additional characteristics based on the one or more determined characteristics of the POI instances. For example, the computer subsystem may be configured to determine die, reticle, field, wafer, and/or lot levels of variation in the one or more characteristics such as CD. On a product die, such calculations may focus on patterns considered to be in the "weak" spectrum, and such patterns may be identified in any suitable manner know in the art. In addition, as described herein, the inspection system may be used to guide the output acquisition subsystem functions. In this manner, conventional defect scans can be augmented with the new scan type. Selection of the POI and care area selection (POI instances) used in the embodiments described herein may also be performed based on area coverage (e.g., observability to process variable impact) and pattern deviation mechanism coverage (e.g., pullback, spacing, width, etc.). In addition, the embodiments described herein can be configured for stratified sampling on the output acquisition subsystem. For example, the detected defects may be optionally sampled as a class. The remainder of the POI instances may be sampled per new metrics or randomly, and the computer subsystem may determine the border between random and metric-based sampling.

Some embodiments described herein are configured for multi-stage data reduction and sampling. These embodiments provide an architecture and method for data reduction and sampling using a complex sampling engine. Rather than simplistic sampling engines that are based on a few parameters, the embodiments described herein involve sophisticated data reduction, machine learning, and use of output to drive subsequent operations in both feedback and feedforward analysis. Subsequent analysis may include any of that described herein including, but not limited to, metrology, SEM review, wafer inspection, and reporting.

Currently, defect sampling for review is generally performed either by random sampling or some biased sampling based on size, location, or optical or electron beam attributes. While such sampling may be sufficient for defect review, sampling tor metrology requires more sophisticated approaches. To address such needs, a new sampling method and engine has been developed without adding complexity to user experience.

A disadvantage of the currently used method is that the sampling does not reflect sites that are likely to have metrology issues. Subtle but important pattern deformation such as CD changes may be overlooked by the sampling. Small changes in patterns are now considered critical to device performance for advanced nodes, but there is no easy way to filter and to sample those sites accordingly using currently available methods. In contrast, the embodiments described herein may incorporate both machine learning and data collection from only the relevant areas. Data are collected from optically relevant areas and machine learning takes a substantially high volume of data set.

In one embodiment, the computer subsystem is configured for determining one or more relationships between one or more of the characteristics of the output of the inspection system and the one or more characteristics of the POI and determining one or more parameters used for the selecting based on the one or more relationships. The relationship(s) may be correlation(s) among response and independent variables. For example, in one embodiment, the relationship (s) between the one or more of the characteristics of the output of the inspection system and the one or more characteristics of the POI include a linear correlation. In another embodiment, the relationship(s) between the one or more of the characteristics of the output of the inspection system and the one or more characteristics of the POI include a non-linear correlation. The linear and/or non-linear correlation may include any suitable such correlations known in the art. The retationship(s) can be defined by algorithms such as random forest or detaining. In this manner, the embodiments described herein may identify critical parameters for sampling. For example, using the new sampling described herein, relevant sampling parameters can be selected from substantially high volume of data types (e.g., a substantially high volume of wafer inspection and metrology data) to improve the sampling of more critical sites with a higher degree of confidence. In one such example, through data analysis, a parameter may be identified from hundreds of potential candidates that impacts the correlations, For instances, it may be determined that XY coordinates relative to die may not be useful while magnitude of signal response may have a relatively high correlation to a response variation. However, the list of critical parameters (useful parameters that define a correlation) may not be static from one data set to another, and therefore the system may determine the critical parameters dynamically for a given data set. Using the embodiments described herein and their new approaches, a user has a much better chance of identifying pattern types and sites that are impacted by poor patterning. Identifying key parameters and efficient sampling improve the value of both inspection and defect review systems.

In some embodiments, determining the one or more relationships is performed using machine learning. In this manner, the embodiments described herein may define relationships correlations) among response and independent variables through machine learning For example, the embodiments described herein may use machine learning to build a model that defines relationships between the characteristic(s) of the output and the characteristic(s) of the POI, The model can then be used for sampling, Therefore, the embodiments described herein may use machine learning to define the relationships. For example, the embodiments described herein provide a dynamic approach to identification of key parameters using hundreds of input candidates. In this manner, sampling may be dynamically controlled based on machine learning and data characteristics. In addition, the embodiments described herein can use machine learning to identify key parameters in the absence of user input automatically. In this manner, the embodiments described herein provide an automated complex sampling engine. The embodiments also provide an architecture that can work as a "black box" that generates sampling results based on criticality and relevance. For example, the architecture described herein provides data reduction and sampling that is not dependent on and transparent to the user.

In another embodiment, the computer subsystem is configured for performing data reduction on the output of the inspection system for the at least the majority of instances of the POI used for determining the one or more relationships by identifying a first portion of the at least the majority of instances, the first portion includes fewer than all of the at least the majority of the instances, and determining the one or more relationships is performed based on only the one or more characteristics of the output generated by the inspection system for the first portion of the at least the majority of instances. The data reduction may include stratified sampling. For example, in the first step of data reduction, certain optical or electron beam parameters such as brightness, contrast, polarity, etc. may be used. This can be performed either by random sampling, biased sampling based on one or more parameters, or stratified sampling across one or more parameters. In particular, 100 data points may be sorted by brightness. One can then take every fifth point to collect a sample. In a similar fashion, the same data can be sorted by combinations of multiple parameters, and stratified sampling can be applied. In this manner, the embodiments described herein may be configured for data selection, data reduction, data sampling, and data prioritization.

In one such example, the embodiments described herein may create a specimen level prequalification step to determine the feasibility of sampling using a multi-stage sampling engine. For example, the prequalification step may include taking a smaller sample of data to learn relevant parameters/attributes that impact a response variable, Once feasible relationships are established, the data set is qualified to move to the subsequent step of sampling.

Multi-stage data sampling may involve a learning stage where an initial set of parameters are determined while removing irrelevant data and then applying the learning to a larger set of data for subsequent sampling. In addition, results of such data selection, data reduction, data sampling, and data prioritization may be fed forward and backward to the machine learning and other steps such as data reduction described herein. In this manner, the embodiments described herein may include machine learning to define relationships based on a relatively small sample of data produced by data reduction, prioritization, and identification of critical parameters. Therefore, the embodiments described herein provide a complex sampling engine with multi-stage data reduction that allows learning of data characteristics dynamically and triggering the next operation accordingly in response to the learned behavior.

In an additional embodiment, the computer subsystem is configured for performing data reduction on the output of the inspection system for the at least the majority of the instances of the POI used for determining the one or more relationships by identifying a first portion of the output of the inspection system for the at least the majority of instances that is optically relevant and eliminating a second portion of the output of the inspection system for the at least the majority of the instances that is not optically relevant, and the first portion of the output of the inspection system includes the output of the inspection system corresponding to actual defects in the instances of the POI. For example, when data are collected for each defect, the signal may be collected from a larger area e.g., 32 pixels by 32 pixels) than the area of the defect. Therefore, the area of the data may be reduced. For instance, the data can be reduced to only 3 pixels by 3 pixels or by taking the ratio of signal coming from the center few pixels to a wider area to see if the signal is actually higher than the background. As such, the embodiments described herein may use only optically or electron beam relevant data for data reduction and sampling, where the optically or electron beam relevant data includes data for defects that are visible and that the data has optical or electron beam signal for. In other words, the data reduction may include identifying optically or electron beam relevant data. In this manner, the embodiments described herein may be configured for data selection, data reduction, data sampling, and data prioritization. In addition, results of such data selection, data reduction, data sampling, and data prioritization may be fed forward and backward to the machine learning and other steps such as data reduction described herein. In one such example, an initially high volume of data may be taken and the data may be reduced to keep the optically or electron beam relevant data (such as real defects, pattern failures, etc.), which may then be fed into machine learning to identify relationships. Through machine learning, key parameters may be automatically determined to further optimize the data. Therefore, the optically or electron beam relevant data may be determined prior to machine learning. As such, the embodiments described herein provide a complex sampling engine with multi-stage data reduction that allows learning of data characteristics dynamically and triggering the next operation accordingly in response to the learned behavior.

In some embodiments, the computer subsystem is configured for determining one or more characteristics of the one or more relationships, and determining the one or more parameters used for the selecting is performed based on the one or more characteristics of the one or more relationships. In one such example, in multi-stage sampling, it may be determined that the initial learning step may or may not prove useful. If a useful relationship between response variables metrology) and independent variables (optical or electron beam attributes) cannot be established, the system will determine whether to continue machine learning (models such as random forest) or to divert to more simple models such as linear correlation or in worst case scenario to resort to random sampling. For example, if the correlation from the learning step is substantially poor, it may be better to use random sampling. However, rather than a user determining this manually, the system may automatically determine which method to use.

In another embodiment, the one or more parameters used for the selecting include a type of the selecting to be performed. For example, the embodiments described herein create a robust determination when the dynamic approach has failed and automatically tune for the most effective method. In one such example, as described herein, the machine learning may be performed to build a model that describes relationship(s) between characteristic(s) of the output and characteristic(s) of the POI. The results of that model building may be used to determine if the model explains the data that is available to the embodiments sufficiently. If it is determined that the model does not sufficiently explain the data, then simplified sampling such as random or attribute based sampling may be performed instead of using the built model. If it is determined that the model does sufficiently explain the data, then machine learning to determine model-based data reduction and sampling on the parent population may be performed. The model may then be stored for subsequent wafers. When subsequent data becomes available, the developed model may be applied to the subsequent data to thereby perform model-based sampling.

In a further embodiment, the one or more parameters used for the selecting include which of the characteristics of the output of the inspection system are used for the selecting. For example, the sampling may perform data reduction that is based on many attributes including, hut not limited to, frequency, density, distribution, yield criticality, and device impact. In particular, there may be 100+ parameters that describe a defect. Simpler such parameters are size, brightness, contrast, and the like. However, there are multitudes of parameters/optical (or electron beam) attributes that are being generated and through the new sampling described herein, relevant parameters that impact response variables can be selected by the system.

Various functions described above may be combined to form a comprehensive strategy for creating and using relatively complex sampling engines. For example, as described further above, the computer subsystem may acquire a substantially high volume of data (e.g., a parent population). The computer subsystem may then take a smatter sample of data (which may be percentage or count based) for initial learning or training of a model). The computer subsystem may then determine parameters that impact the response variable. In parallel, data may be reduced if there are data points that do not have enough signal. If the training provides a sufficient relationship among response variables and independent variables, the model is generated. In this step, a machine learning algorithm may be used. If there is insufficient correlation, the system may opt for a simpler sampling approach such as random or simpler biased sampling (e.g., pick defects with relatively high contrast or other attributes). If modeling shows sufficient correlation, then the computer subsystem may automatically apply the model to the parent population to generate sampling. All of the learning, model generation, and deployment is performed automatically while data is being collected by the output acquisition subsystem.

The embodiments described herein provide relatively complex sampling engines. For example, the embodiments can be used to reduce the data volume while increasing the data relevance. In addition, the embodiments described herein provide the ability to feed forward useful commands. Furthermore, the embodiments described herein provide the ability to monitor and control the sampling that is performed.

As an alternative to the embodiments described herein, lots of iterative manual work may be performed using non-integrated tools and moving data from one system to another which also requires costly user intervention. It is not practical to require users to perform all of that analysis.

Each of the embodiments of the system described above may be combined together into one single embodiment. In other words, unless otherwise noted herein, none of the system embodiments are mutually exclusive of any other system embodiments.

Another embodiment relates to a computer-implemented method for determining one or more characteristics of a POI on a specimen. The method includes acquiring output of an inspection system generated by the inspection system for at least a majority of instances of a POI on a specimen and stored in a computer-readable storage medium. The inspection system acquires the output at a resolution that is lower than a resolution of an output acquisition subsystem. The inspection system stores the output acquired at the at least the majority of instances regardless of characteristics of the output. The output acquisition subsystem includes at least an energy source and a detector. The output acquisition subsystem is configured to direct energy generated by the energy source to the specimen while the detector detects energy from the specimen and generates output responsive to the detected energy.

The method also includes selecting one or more of the at least the majority of instances at which the output is generated by the output acquisition subsystem. The selecting is performed based on the characteristics of the output of the inspection system. In addition, the method includes acquiring the output generated by the output acquisition subsystem for the selected one or more of the at least the majority of instances. The resolution of the output acquisition subsystem with which the output is acquired at the selected one or more of the at least the majority of instances is higher than the resolution of the inspection system. In addition, the method includes determining one or more characteristics of the POI based on the output of the output acquisition subsystem at the selected one or more of the at least the majority of instances. Acquiring the output of the inspection system, selecting the one or more of the at least the majority of instances, acquiring the output generated by the output acquisition subsystem, and determining the one or more characteristics are performed by a computer subsystem coupled to the output acquisition subsystem. The computer subsystem includes one or more processors configured to execute instructions from a memory medium.

Each of the steps of the method may be performed as described further herein. The method may also include any other step(s) that can be performed b the inspection subsystem and/or computer subsystem(s) described herein. In addition, the method described above may be performed by any of the system embodiments described herein.

Figure 2:
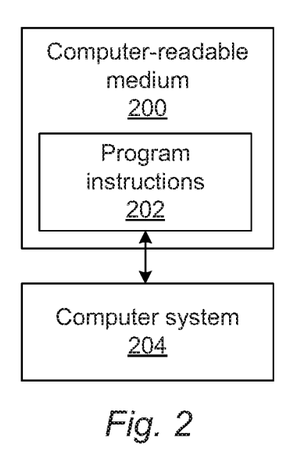
FIG. 2 is a block diagram illustrating one embodiment of a non-transitory computer-readable medium storing program instructions for causing a computer system to perform a computer-implemented method described herein.

An additional embodiment relates to a non-transitory computer-readable medium storing program instructions executable on a computer system for performing a computer-implemented method for determining one or more characteristics of a POI on a specimen. One such embodiment is shown in FIG. 2. In particular, as shown in FIG. 2, non-transitory computer-readable medium 200 stores program instructions 202 executable on computer system 204. The computer-implemented method may include any step(s) of any method(s) described herein.

Program instructions 202 implementing methods such as those described herein may be stored on computer-readable medium 200. The computer-readable medium may be a storage medium such as a magnetic or optical disk, a magnetic tape, or any o or suitable non-transitory computer-readable medium known in the art.

The program instructions may be implemented in any of various ways, including procedure-based techniques, component-based techniques, and/or object-oriented.

techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system 204 may be configured according to any of the embodiments described herein.

Further modifications and alternative embodiments of various aspects of the invention will be apparent to those skilled in the art in view of this description. For example, methods and systems for determining one or more characteristics of a POI on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized. independently, all as would be apparent to one skilled in the art after having the benefit of this description of the invention. Changes may be made in the elements described herein without departing from the spirit and scope of the invention as described in the following claims.

What is claimed is:

1. A system configured to determine one or more characteristics of a pattern of interest on a specimen, comprising:
    an output acquisition subsystem comprising at least an energy source and a detector, wherein the output acquisition subsystem is configured to direct energy generated by the energy source to a specimen while the detector detects energy from the specimen and generates output responsive to the detected energy, and wherein the specimen is a wafer; and
    a computer subsystem comprising one or more processors configured to execute instructions from a memory medium, wherein the computer subsystem is configured for:
        acquiring output of an inspection system generated by the inspection system for at least a majority of instances of a pattern of interest formed on the specimen and stored in a computer-readable storage medium, wherein the inspection system is an optical or electron beam inspection system, wherein the output of the inspection system comprises images of the pattern of interest formed on the specimen generated by one or more detectors of the optical or electron beam inspection system while the specimen is being scanned by the inspection system, wherein the one or more detectors of the optical or electron beam inspection system generate the output of the inspection system at a resolution that is lower than a resolution with which the detector of the output acquisition subsystem generates the output of the output acquisition subsystem, and wherein the inspection system stores the output acquired at the at least the majority of instances regardless of characteristics of the output of the inspection system;
        selecting one or more of the at least the majority of instances at which the output is generated by the output acquisition subsystem, wherein said selecting is performed based on the characteristics of the output of the inspection system;
        acquiring the output generated by the output acquisition subsystem for the selected one or more of the at least the majority of instances, wherein the resolution of the output acquisition subsystem with which the output of the output acquisition subsystem is generated by the detector of the output acquisition subsystem at the selected one or more of the at least the majority of instances is higher than the resolution at which the one or more detectors of the inspection system generate the output of the inspection system; and
        determining one or more characteristics of the pattern of interest based on the output of the output acquisition subsystem at the selected one or more of the at least the majority of instances.

2. The system of claim 1, wherein the one or more characteristics of the pattern of interest determined based on the output of the output acquisition subsystem are not detectable in any output generated by the inspection system.

3. The system of claim 1, wherein the inspection system identities the locations of the at least the majority of the instances of the pattern of interest on the specimen without detecting defects on the specimen, and wherein selecting the one or more of the at least the majority of instances is not performed based on defects detected at the instances of the pattern of interest.

4. The system of claim 1, wherein the instances of the pattern of interest on the specimen are located by the inspection system with sub-pixel accuracy.

5. The system of claim 1, wherein the output for the selected one or more of the at least the majority of instances is generated by the output acquisition subsystem by locating the selected one or more of the at least the majority of instances with sub-pixel accuracy.

6. The system of claim 1, wherein said determining the one or more characteristics is performed based on the output of the output acquisition subsystem at the selected one or more of the at least the majority of instances in combination with the output of the inspection system generated for at least one of the instances of the pattern of interest.

7. The system of claim 1, wherein said determining the one or more characteristics comprises determining one or more initial values for the one or more characteristics of the pattern of interest based on the output of the output acquisition subsystem at the selected one or more of the at least the majority of instances in combination with a first portion of the output of the inspection system generated for at least one of the instances of the pattern of interest and, based on the one or more initial values, selecting a second portion of the output of the inspection system generated for at least one of the instances of the pattern of interest stored in the computer-readable storage medium and determining the one or more characteristics of the pattern of interest based on the output of the output acquisition subsystem at the selected one or more of the at least the majority of instances in combination with the second portion of the output of the inspection system generated for the at least one of the instances of the pattern of interest.

8. The system of claim 1, wherein the computer subsystem is further configured for determining a variation in the one or more characteristics of the pattern of interest and determining a source of the variation based on the variation.

9. The system of claim 1, wherein the determined one or more characteristics of the pattern of interest correspond to only patterning deviations in the pattern of interest.

10. The system of claim 1, wherein the characteristics of the output of the inspection system comprise characteristics of raw image data generated by the inspection system for the at least the majority of instances of the pattern of interest.

11. The system of claim 1, wherein the computer subsystem is further configured for determining one or more relationships between one or more of the characteristics of the output of the inspection system and the one or more characteristics of the pattern of interest and determining one or more parameters used for the selecting based on the one or more relationships.

12. The system of claim 11, wherein determining the one or more relationships is performed using machine learning.

13. The system of claim 11, wherein the computer subsystem is further configured for performing data reduction on the output of the inspection system for the at least the majority of instances of the pattern of interest used for determining the one or more relationships by identifying a first portion of the at least the majority of instances, wherein the first portion includes fewer than all of the at least the majority of the instances, and wherein determining the one or more relationships is performed based on only the one or more characteristics of the output generated by the inspection system for the first portion of the at least the majority of instances.

14. The system of claim 11, wherein the computer subsystem is further configured for performing data reduction on the output of the inspection system for the at least the majority of the instances of the pattern of interest used for determining the one or more relationships by identifying a first, portion of the output of the inspection system for the at least the majority of instances that is optically relevant and eliminating a second portion of the output of the inspection system for the at least the majority of instances that is not optically relevant, and wherein the first portion of the output of the inspection system comprises the output of the inspection system corresponding to actual defects in the instances of the pattern of interest.

15. The system of claim 11, wherein the computer subsystem is further configured for determining one or more characteristics of the one or more relationships, and wherein determining the one or more parameters used for the selecting is performed based on the one or more characteristics of the one or more relationships.

16. The system of claim 15, wherein the one or more parameters used for the selecting comprise a type of the selecting to be performed.

17. The system of claim 11, wherein the one or more parameters used for the selecting comprise which of the characteristics of the output of the inspection system are used for the selecting.

18. The system of claim 11, wherein the one or more relationships comprise a linear correlation between the one or more of the characteristics of the output of the inspection system and the one or more characteristics of the pattern of interest.

19. The system of claim 11, wherein the one or more relationships comprise a non-linear correlation between the one or more of the characteristics of the output of the inspection system and the one or more characteristics of the pattern of interest.

20. The system of claim 1, wherein the determined one or more characteristics of the pattern of interest comprise one or more quantifiable characteristics of the pattern of interest.

21. The system of claim 1, wherein the system is further configured as a metrology system.

22. The system of claim 1, wherein the computer-readable storage medium is configured as a virtual inspector.

23. The system of claim 1, wherein the energy source is a light source, and wherein the energy detected by the detector comprises light.

24. The system of claim 1, wherein the energy source is an electron beam source, and wherein the energy detected by the detector comprises electrons.

25. The system of claim 1, wherein the energy source is a charged particle beam source, and wherein the energy detected by the detector comprises charged particles.

26. A non-transitory computer-readable medium, storing program instructions executable on a computer system for performing a computer-implemented method for determining one or more characteristics of a pattern of interest on a specimen, wherein the computer-implemented method comprises:

acquiring output of an inspection system generated by the inspection system for at least a majority of instances of a pattern of interest formed on a specimen and stored in a computer-readable storage medium, wherein the specimen is a wafer, wherein the inspection system is an optical or electron beam inspection system, wherein the output of the inspection system comprises images of the pattern of interest formed on the specimen generated by one or more detectors of the optical or electron beam inspection system while the specimen is being scanned by the inspection system, wherein the one or more detectors of the optical or electron beam inspection system generate the output of the inspection system at a resolution that is lower than a resolution with which a detector of an output acquisition subsystem generates output of the output acquisition subsystem, wherein the inspection system stores the output acquired at the at least the majority of instances regardless of characteristics of the output, wherein the output acquisition subsystem comprises at least an energy source and the detector, and wherein the output acquisition subsystem is configured to direct energy generated by the energy source to the specimen while the detector detects energy from the specimen and generates the output responsive to the detected energy;

selecting one or more of the at least the majority of instances at which the output is generated by the output acquisition subsystem, wherein said selecting is performed based on the characteristics of the output of the inspection system;

acquiring the output generated by the output acquisition subsystem for the selected one or more of the at least the majority of instances, wherein the resolution of the output acquisition subsystem with which the output of the output acquisition subsystem is generated by the detector of the output acquisition subsystem at the selected one or more of the at least the majority of instances is higher than the resolution at which the one or more detectors of the inspection system generate the output of the inspection system; and determining one or more characteristics of the pattern of interest based on the output of the output acquisition subsystem at the selected one or more of the at least the majority of instances, wherein acquiring the output of the inspection system, selecting the one or more of the at least the majority of instances, acquiring the output generated by the output acquisition subsystem, and determining the one or more characteristics are performed by the computer system, wherein the computer system comprises one or more processors configured to execute the program instructions from the non-transitory computer-readable medium, and wherein the computer system is coupled to the output acquisition subsystem.

27. A computer-implemented method for determining one or more characteristics of a pattern of interest on a specimen, comprising:

acquiring output of an inspection system generated by the inspection system for at least a majority of instances of a pattern of interest on a specimen and stored in a computer-readable storage medium, wherein the specimen is a wafer, wherein the inspection system is an optical or electron beam inspection system, wherein the output of the inspection system comprises images of the pattern of interest formed on the specimen generated by one or more detectors of the optical or electron beam inspection system while the specimen is being scanned by the inspection system, wherein the one or more detectors of the optical or electron beam inspection system generate the output of the inspection system at a resolution that is lower than a resolution with which a detector of an output acquisition subsystem generates output of the output acquisition subsystem, wherein the inspection system stores the output acquired at the at least the majority of instances regardless of characteristics of the output, wherein the output acquisition subsystem comprises at least an energy source and the detector, and wherein the output acquisition subsystem is configured to direct energy generated by the energy source to the specimen while the detector detects energy from the specimen and generates the output responsive to the detected energy;

selecting one or more of the at least the majority of instances at which the output is generated by the output acquisition subsystem, wherein said selecting is performed based on the characteristics of the output of the inspection system;

acquiring the output generated by the output acquisition subsystem for the selected one or more of the at least the majority of instances, wherein the resolution of the output acquisition subsystem with which the output of the acquisition subsystem is generated by the detector of the output acquisition subsystem at the selected one or more of the at least the majority of instances is higher than the resolution at which the one or more detectors of the inspection system generate the output of the inspection system; and determining one or more characteristics of the pattern of interest based on the output of the output acquisition subsystem at the selected one or more of the at least the majority of instances, wherein acquiring the output of the inspection system, selecting the one or more of the at least the majority of instances, acquiring the output generated by the output acquisition subsystem, and determining the one or more characteristics are performed by a computer subsystem coupled to the output acquisition subsystem, and wherein the computer subsystem comprises one or more processors configured to execute instructions from a memory medium.

* * * * *